US009493661B2

United States Patent
Hoffmann et al.

(10) Patent No.: US 9,493,661 B2
(45) Date of Patent: *Nov. 15, 2016

(54) GLYCEROL DIESTERS, METHOD FOR PRODUCING SAME, AND USE OF SAME IN COATINGS MATERIALS

(71) Applicant: BASF Coatings GmbH, Münster (DE)

(72) Inventors: Peter Hoffmann, Senden (DE); Sebastien Porcher, Ludwigshafen (DE); Melanie Goudard, Marseilles (FR)

(73) Assignee: BASF Coatings GmbH, Muenster (DE)

( * ) Notice: Subject to any disclaimer, the term of this patent is extended or adjusted under 35 U.S.C. 154(b) by 74 days.

This patent is subject to a terminal disclaimer.

(21) Appl. No.: 14/358,337

(22) PCT Filed: Nov. 16, 2012

(86) PCT No.: PCT/EP2012/072884
§ 371 (c)(1),
(2) Date: May 15, 2014

(87) PCT Pub. No.: WO2013/072481
PCT Pub. Date: May 23, 2013

(65) Prior Publication Data
US 2014/0315033 A1     Oct. 23, 2014

Related U.S. Application Data

(60) Provisional application No. 61/560,842, filed on Nov. 17, 2011.

(30) Foreign Application Priority Data

Nov. 17, 2011    (EP) .................................. 11189618

(51) Int. Cl.
| | |
|---|---|
| *C09D 7/00* | (2006.01) |
| *B05D 7/00* | (2006.01) |
| *C07C 69/30* | (2006.01) |
| *C09D 4/00* | (2006.01) |
| *C09D 133/00* | (2006.01) |

(52) U.S. Cl.
CPC ............... *C09D 7/001* (2013.01); *B05D 7/572* (2013.01); *C07C 69/30* (2013.01); *C09D 4/00* (2013.01); *C09D 133/00* (2013.01); *Y10T 428/31663* (2015.04)

(58) Field of Classification Search
CPC ........ C07C 69/30; B05D 7/572; C09D 4/00; C09D 7/001; C09D 133/00; Y10T 428/31551; Y10T 428/31663
USPC ............. 428/423.1, 447; 524/853; 427/385.5
See application file for complete search history.

(56) References Cited

U.S. PATENT DOCUMENTS

| | | | | |
|---|---|---|---|---|
| 3,629,295 | A | * | 12/1971 | Stackman et al. ............. 549/557 |
| 4,423,071 | A | | 12/1983 | Chignac et al. |
| 6,187,893 | B1 | | 2/2001 | Bruchmann et al. |
| 6,255,262 | B1 | * | 7/2001 | Keenan et al. ............... 508/486 |
| 2003/0027921 | A1 | | 2/2003 | Speier et al. |

(Continued)

FOREIGN PATENT DOCUMENTS

| | | |
|---|---|---|
| EP | 0908479 | 4/1999 |
| EP | 0994117 | 4/2000 |
| EP | 1115714 | 7/2001 |
| EP | 1273640 | 1/2003 |
| WO | WO-00/17179 | 3/2000 |
| WO | WO-01/09260 | 2/2001 |

(Continued)

OTHER PUBLICATIONS

PCT International Search Report in PCT/EP2012/072884, mailed Dec. 20, 2012, 4 pages.
Van Dijk, J.H., et al., "Analysis of Coatings Additives and Free Monomers Using Liquid and Capillary Gas Chromatography", Akzo Research, Corporate Research Department, 12 pages.

*Primary Examiner* — Thao T Tran
(74) *Attorney, Agent, or Firm* — Servilla Whitney LLC

(57) ABSTRACT

Described are glycerol diesters of the general formula (I)

wherein one of the two radicals $R^1$ or $R^2$ is hydrogen, and the radical of the two radicals $R^1$ and $R^2$ that is not hydrogen is a radical:

and the radicals $R^3$, $R^4$, $R^5$, and $R^6$ independently of one another are a saturated, aliphatic radical having 1 to 20 carbon atoms, with the proviso that the radicals $R^3$ and $R^4$ together contain at least 5 carbon atoms and the radicals $R^5$ and $R^6$ together contain at least 5 carbon atoms. Also described is a process for preparing the glycerol diesters, use thereof as reactive diluents, coating materials comprising the glycerol diesters, multicoat paint systems and their production, comprising the use of the coating materials, and also to substrates coated therewith.

10 Claims, No Drawings

(56) References Cited

U.S. PATENT DOCUMENTS

2008/0124532 A1* 5/2008 Menovcik et al. ............ 428/217
2010/0143596 A1* 6/2010 Groenewolt et al. ......... 427/379
2012/0095244 A1* 4/2012 Gouman et al. .............. 549/515
2014/0023789 A1 1/2014 Groenewolt et al.
2014/0295198 A1* 10/2014 Hoffmann et al. ........... 428/523

FOREIGN PATENT DOCUMENTS

| WO | WO-2007/074333 | 7/2007 |
| WO | WO-2008/074489 | 6/2008 |
| WO | WO-2008/074490 | 6/2008 |
| WO | WO-2008/074491 | 6/2008 |

\* cited by examiner

GLYCEROL DIESTERS, METHOD FOR PRODUCING SAME, AND USE OF SAME IN COATINGS MATERIALS

CROSS-REFERENCE TO RELATED APPLICATIONS

This application is the National State entry of PCT/EP2012/072884, filed on Nov. 16, 2012, which claims priority to U.S. Provisional Application Ser. No. 61/560,842, filed on Nov. 17, 2011 and European Patent Application No. 11189618.9, filed on Nov. 17, 2011, the disclosures of which are incorporated herein by reference in their entireties.

TECHNICAL FIELD

The present invention relates to glycerol diesters, their preparation and use, and also to coating material compositions comprising such glycerol diesters. The invention further relates to multicoat paint systems obtained using the coating material compositions, and to a method for producing such multicoat paint systems, and to substrates painted therewith.

BACKGROUND

There is a continual demand for paints which are eco-friendly and emit less solvent. An increase in demand exists in particular for low-solvent coating materials. One way of lowering the solvent content in coating materials is to select therein solvents which have a particularly effectively diluting effect, i.e. viscosity-lowering effect. This way is often associated with the use of binders which are of low molecular mass and therefore generally less viscous. Despite this development, low levels of volatile organic compounds (VOCs for short) are difficult to achieve without adverse effect on the appearance of the finish.

Another way of obtaining coating materials having a low VOC content is to use what are called reactive diluents. These are solvents which by chemical reaction with at least one crosslinking agent or binder that remains in the cured paint are incorporated into the paint film. The VOC content is therefore not increased.

Thus, there is a need for new reactive diluents which not only possess a good diluting effect but also enhance the appearance of the cured finish and ensure effective leveling.

SUMMARY

A first aspect of the present invention is directed to a glycerol diester. In a first embodiment, a glycerol diester is of general formula (I)

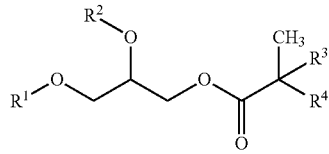

wherein one of the two radicals $R^1$ or $R^2$ is hydrogen and the radical of the two radicals $R^1$ and $R^2$ that is not hydrogen is a radical

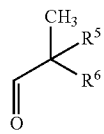

and the radicals $R^3$, $R^4$, $R^5$ and $R^6$ independently of one another are a saturated, aliphatic radical having 1 to 20 carbon atoms, with the proviso that the radicals $R^3$ and $R^4$ together contain at least 5 carbon atoms and the radicals $R^5$ and $R^6$ together contain at least 5 carbon atoms.

In a second embodiment, the glycerol diester of the first embodiment is modified, wherein $R^1$ is hydrogen.

In a third embodiment, the glycerol diester of the first embodiment is modified, wherein $R^2$ is hydrogen.

In a fourth embodiment, the glycerol diester of the first through third embodiments is modified, wherein the radicals $R^3$ and $R^4$ together contain 4 to 10 carbon atoms and the radicals $R^5$ and $R^6$ together contain 4 to 10 carbon atoms.

A second aspect of the present invention is directed to a process for preparing glycerol diesters. In a fifth embodiment, a process for preparing the glycerol diesters of one or more of the first through fourth embodiments, comprises reacting a compound of the general formula (II)

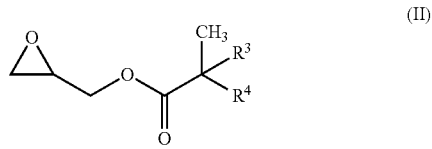

with a compound of the general formula (III)

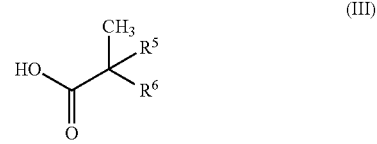

by ring-opening addition of the COOH group of the compound of the formula (III) to the epoxy group of the compound of the formula (II).

In a sixth embodiment, the process of the fifth embodiment is modified, wherein the compound of the general formula (II) is a glycidyl ester of neodecanoic acid and the compound of the general formula (III) is neodecanoic acid.

A third aspect of the present invention is directed to a method of preparing a composition. In a seventh embodiment, a method of preparing a composition comprises adding a reactive diluent comprising the glycerol disaster of the first through fourth embodiments to a coating material composition, an adhesive, or a sealant.

In an eighth embodiment, the method of claim 7 is modified, wherein the coating material composition is a clearcoat material.

A fourth aspect of the present invention is directed to a coating material composition. In a ninth embodiment, a coating material composition comprises (a) at least one polymeric polyol selected from the group consisting of poly(meth)acrylate polyols, polyester polyols, polyurethane polyols, and polysiloxane polyols, (b) at least one aliphatic polyisocyanate and (c) the glycerol diester of the first through fourth embodiments.

In a tenth embodiment, the coating material composition of the ninth embodiment is modified, wherein (a) comprises at least one poly(meth)acrylate polyol.

In an eleventh embodiment, the coating material composition of the ninth and tenth embodiments is modified, wherein the hydroxyl number of component (a) differs by not more than 20% from the hydroxyl number of the glycerol diester component (c) used in the coating material composition, and/or the fraction of the glycerol diester component (c) is 2% to 20% by weight, based on the total weight of components (a) plus (c).

A fifth aspect of the present invention is directed to a multicoat paint system. In a twelfth embodiment, a multicoat paint system comprises at least two coats which are disposed on a substrate, wherein the uppermost coat of the at least two coats is composed of the coating material composition of the ninth through eleventh embodiments.

A sixth aspect of the present invention is directed to a method for producing a multicoat paint system. In a thirteenth embodiment, a method for producing a multicoat paint system comprises (i) applying a primer-surfacer coating material to an untreated or pretreated substrate and applying at least one basecoat composition thereto, or (ii) applying at least one basecoat composition to an untreated or pretreated substrate; and subsequently (iii) applying at least one clearcoat composition, the clearcoat composition comprising the coating composition the ninth through eleventh embodiments, followed by (iv) curing of the multicoat paint system at a temperature of up to 100° C. maximum.

In a fourteenth embodiment, the method of the thirteenth embodiment is modified, wherein step (iv) is carried out at a temperature of 30 to 60° C.

A seventh aspect of the present invention is directed to a substrate. A fifteenth embodiment is directed to a substrate that has been coated with the multicoat paint system of the twelfth embodiment.

A sixteenth embodiment is directed to a substrate that has been coated by the method of the thirteenth and fourteenth embodiments.

DETAILED DESCRIPTION

Described are new glycerol diesters of the general formula (I)

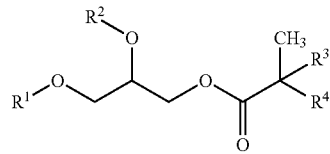

wherein
one of the two radicals $R^1$ or $R^2$ is hydrogen and the radical of the two radicals $R^1$ and $R^2$ that is not hydrogen is a radical

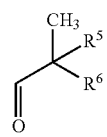

and
the radicals $R^3$, $R^4$, $R^5$ and $R^6$ independently of one another are a saturated, aliphatic radical having 1 to 20 carbon atoms, specifically 1 to 10 carbon atoms,
with the proviso that the radicals $R^3$ and $R^4$ together contain at least 5 carbon atoms and the radicals $R^5$ and $R^6$ together contain at least 5 carbon atoms.

In one or more embodiments, the joint number of carbon atoms in the radicals $R^3$ and $R^4$ and the joint number of carbon atoms in the radicals $R^5$ and $R^6$ is not more than 18, specifically 4 to 10 and very specifically 4 to 8.

Aside from the above proviso, in one or more embodiments, the radicals $R^3$, $R^4$, $R^5$ and $R^6$ are independently of one another, alkyl radicals having 1 to 10, more specifically 1 to 8 and very specifically 1 to 6 carbon atoms. These alkyl radicals may be substituted or unsubstituted and, in specific embodiments, are unsubstituted. These alkyl radicals may be linear or branched.

Where these alkyl radicals are substituted, substituents present are one or more radicals selected from the group consisting of hydroxyl groups, $O(CO)_nR^9$ groups with $n=0$ or 1 and $R^9$=branched or unbranched alkyl having 1 to 6 carbon atoms, and aliphatic radicals containing ether groups and/or ester groups and having 1 to 10, specifically 2 to 10 carbon atoms.

These compounds of the general formula (I) are referred to below as "glycerol diesters of the invention".

Further provided by the invention is a process for preparing the glycerol diesters of the above-indicated general formula (I).

The glycerol diesters of the above-indicated formula (I) are obtainable by reacting a compound of the general formula (II)

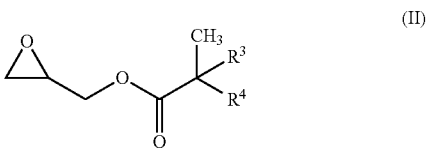

with a compound of the general formula (III)

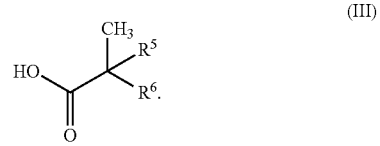

The reaction takes place by ring-opening addition of the COOH group of the compound of the formula (III) to the epoxy group of the compound of the formula (II).

The radicals $R^3$, $R^4$, $R^5$ and $R^6$ are defined as described above for the glycerol diester of the invention.

The process for preparing the glycerol diesters of the invention is also referred to below as "inventive preparation of the glycerol diesters".

The ring opening may take place with formation of a primary hydroxyl group or a secondary hydroxyl group. Where a primary hydroxyl group is obtained, in the compounds of the general formula (I), $R^1$=hydrogen and the radical $R^2$=a radical of the formula $O=C-C(CH_3)(R^5)(R^6)$. Where a secondary hydroxyl group is obtained, in the compounds of the general formula (I), $R^2$=hydrogen and $R^1$=a radical of the formula $O=C-C(CH_3)(R^5)(R^6)$.

The reaction product formed generally comprises mixtures of compounds of the general formula (I), with some of the products carrying primary hydroxyl groups and the remainder having secondary hydroxyl groups. The ratio of primary to secondary hydroxyl groups can be influenced through the reaction conditions, more particularly the reaction temperature and the use of catalysts. Without use of a catalyst, the fraction of compounds with primary hydroxyl groups is generally predominant. Where, for example, ethyltriphenylphosphonium iodide is used as catalyst, the ratio of secondary to primary can be raised.

By controlling the ratio of primary to secondary hydroxyl groups it is possible to a certain extent to influence the reactivity of the reactive diluent. Since compounds of the general formula (I) that contain primary hydroxyl groups generally react more quickly than those with secondary hydroxyl groups, it is possible to control their reactivity, with respect to isocyanate groups, for example, through the reaction regime during the preparation of the compounds of the general formula (I). This advantageous flexibility to the process opens up the possibility of obtaining custom-tailored glycerol diesters of the invention and hence of influencing the pot life of the coating materials which comprise the glycerol diesters of the invention.

The compounds of the general formula (II) can be obtained, for example, by reacting epichlorohydrin with a carboxylic acid $R^3R^4(CH_3)C$—COOH as described in EP 1 115 714 B1 (example 1). In one or more embodiments, one reaction product which falls within the general formula (II) and can be employed is the glycidyl ester of Versatic® acid, which is obtainable under the trade name Cardura® E10.

Carboxylic acids $R^3R^4(CH_3)C$—COOH and hence also carboxylic acids of the analogously defined general formula (III) are available commercially. Particularly preferred among them are the highly branched, saturated monocarboxylic acids with relatively long side chains and tertiary COOH groups, which are known by the name Versatic® acids and are formed, for example, by Koch carboxylic acid synthesis from olefins, carbon monoxide and water. Especially preferred among these is neodecanoic acid.

The glycerol diesters of the invention can be prepared, for example, by introducing the compounds of the general formulae (II) and (III) into a solvent and heating this initial charge to a temperature in the range from 100 to 160° C. If low-boiling solvents are used, the reaction may be carried out under elevated pressure. The reaction progress is monitored by determination of the acid number. Examples of suitable solvents include aromatic hydrocarbons such as xylene, toluene, solvent naphtha, esters such as butyl acetate, pentyl acetate, ether esters such as methoxypropyl acetate, ethoxyethyl propionate, ketones such as methyl ethyl ketone, methyl isoamyl ketone and methyl isobutyl ketone. The glycerol diesters of the invention obtained in this way may then be used, if desired following (partial) removal of the solvent, in the coating material compositions of the invention.

The glycerol diesters of the invention may alternatively be formed in situ, in other words without being isolated, before or during the synthesis of the polymeric polyols (a), more particularly of the hydroxyl-containing poly(meth)acrylate. This can be accomplished, for example, by introducing the compounds of the general formulae (II) and (III) into a suitable solvent, heating this initial charge to a temperature of, for example, 80 to 180° C., 160° C. for example, and subsequently metering in the catalysts and monomers that form the polymeric polyol (a). Suitable catalysts, where the polymeric polyol (a) is a hydroxyl-containing poly(meth)acrylate, are, for example, peroxide catalysts, such as di-tert-butyl peroxide (DTBP), for example. With this embodiment it is possible only to use monomer mixtures which include only minor fractions (<10% by weight, based on the total weight of all the monomers) of acid-functional and/or epoxide-functional monomers. The reaction may take place under atmospheric or superatmospheric pressure. Suitable solvents may be added to the reaction mixture before, during or after the polymerization, in order to influence on the one hand the polymerization reaction and on the other hand the resulting viscosity. Before, during or after the polymerization it is possible to add small amounts (0.01-2.0% by weight, based on the total amount of the solid polymer) of a suitable reducing agent, in order to give particularly light-colored resin solutions. In one or more embodiments, the reducing agents used are y alkyl phosphites; triisodecyl phosphite is used in specific embodiments.

The present invention also provides for the use of the glycerol diesters of the invention in coating material compositions, adhesives and sealants as reactive diluents. In one or more embodiments, these coating material compositions, adhesives and sealants comprise compounds having one or more groups that are reactive toward the hydroxyl groups of the glycerol diester of the invention, such as, for example, isocyanate groups or the reactive groups on amino resins or triazines such as TACT. The compounds that are reactive toward the hydroxyl groups in the coating material compositions, adhesives and sealants are those known as crosslinking agents and/or binders. In one or more embodiments, the glycerol diesters of the invention are used as reactive diluents in coating material compositions, more particularly topcoat materials, and very specifically clearcoat materials. In these systems they not only develop a viscosity-lowering effect but also lead in general to coatings having improved leveling. Specific embodiments are directed to the use of the glycerol diesters of the invention as reactive diluents and leveling agents.

Further provided by the invention is a coating material composition comprising
(a) at least one polymeric polyol selected from the group consisting of poly(meth)acrylate polyols, polyester polyols, polyurethane polyols and polysiloxane polyols,
(b) at least one aliphatic polyisocyanate and
(c) at least one glycerol diester of the general formula (I)

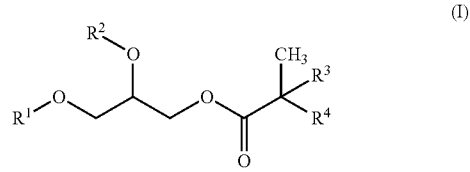

wherein
one of the two radicals $R^1$ or $R^2$ is hydrogen and the radical of the two radicals $R^1$ and $R^2$ that is not hydrogen is a radical

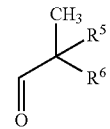

and
the radicals $R^3$, $R^4$, $R^5$ and $R^6$ independently of one another are a saturated, aliphatic radical having 1 to 20, specifically 3 to 10 carbon atoms,
with the proviso that the radicals $R^3$ and $R^4$ together contain at least 5 carbon atoms and the radicals $R^5$ and $R^6$ together contain at least 5 carbon atoms.

Specific definitions of the radicals $R^3$, $R^4$, $R^5$ and $R^6$ are found above in relation to the glycerol diester of the invention.

The coating material composition of the invention is also referred to for short below as "coating material of the invention".

A "polymeric polyol" herein means a polyol having at least two hydroxyl groups, the term "polymeric" herein also encompassing the term "oligomeric". Oligomers herein are composed of at least three monomer units.

In one or more embodiments, the polymeric polyols (a) have weight-average molecular weights $M_w$>500 daltons, measured by means of GPC (gel permeation chromatography) against a polystyrene standard, specifically of 800 to 100 000 daltons, more particularly of 1000 to 50 000 daltons. In specific embodiments, the polymeric polyols (a) are those having a weight-average molecular weight of 1000 to 10 000 daltons.

In one or more embodiments, the polymeric polyols (a) have a hydroxyl number (OH number) of 30 to 400 mg KOH/g, more particularly of 100 to 300 mg KOH/g, and very particularly of 120 to 180 mg KOH/g.

In one specific embodiment of the coating material composition of the invention, the OH number of the polymeric polyol (a) or of the mixture of polymeric polyols (a) differs by not more than 20% and very specifically by not more than 10% from the OH number of the glycerol diester component (c) used in the coating material composition.

The glass transition temperatures of the polymeric polyols (a), measured by DSC (differential scanning calorimetry, TA Instruments DSC 1000 from Waters GmbH, Eschborn; heating rate 10° C./minute), are, in one or more embodiments, between −150 and 100° C., more specifically between −120° C. and 80° C.

As used herein, the term "poly(meth)acrylate" refers to not only polyacrylates but also polymethacrylates, and also polymers which comprise both methacrylates and/or methacrylic acid and acrylates and/or acrylic acid. Besides acrylic acid, methacrylic acid and/or the esters of acrylic acid and/or methacrylic acid, the poly(meth)acrylates may also comprise other ethylenically unsaturated monomers. In one or more embodiments, the monomers from which the poly(meth)acrylates are obtained are monoethylenically unsaturated monomers. A "poly(meth)acrylate polyol" refers to a poly(meth)acrylate which contains at least two hydroxyl groups.

Instead of or in addition to the poly(meth)acrylate polyols, it is also possible to use polyester polyols. A polyester polyol here is a polyester which carries at least two hydroxyl groups.

In the case of joint use of poly(meth)acrylate polyols and polyester polyols, both components may be prepared individually or by polymerizing the poly(meth)acrylate polyol in situ in a polyester polyol component or solution thereof in an appropriate solvent.

Especially preferred among the polymeric polyols are polyacrylate polyols and/or polymethacrylate polyols and also their copolymers. They may be prepared in a single stage or a multiplicity of stages. They may also be present in the form, for example, of random polymers, gradient copolymers, block copolymers or graft polymers.

The poly(meth)acrylate polyols that are especially preferred in accordance with the invention are generally copolymers with other vinylically unsaturated monomers, and preferably have weight-average molecular weights $M_w$ of 1000 to 20 000 g/mol, more particularly of 1500 to 10 000 g/mol, measured in each case by means of gel permeation chromatography (GPC) against a polystyrene standard.

The glass transition temperature of the poly(meth)acrylate polyols is generally between −100 and 100° C., more particularly between −50 and 80° C. (measured by means of DSC measurements, as indicated above).

In one or more embodiments, the poly(meth)acrylate polyols have an OH number of 60 to 250 mg KOH/g, more particularly 70 to 200 mg KOH/g and very particularly 120 to 180 mg KOH/g. In one or more embodiments, their acid number is 0 to 30 mg KOH/g.

The hydroxyl number indicates the number of mg of potassium hydroxide that are equivalent to the amount of acetic acid bound by 1 g of substance on acetylation. The sample is boiled with acetic anhydride-pyridine for the determination, and the resulting acid is titrated with potassium hydroxide solution (DIN 53240-2).

The acid number herein indicates the number of mg of potassium hydroxide consumed in the neutralization of 1 g of the compound in question (DIN EN ISO 2114).

Hydroxyl-containing monomer units of the poly(meth)acrylate polyols that are used in one or more embodiments are one or more hydroxyalkyl(meth)acrylates, such as, more particularly, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, and also, in particular, 4-hydroxybutyl acrylate and/or 4-hydroxybutyl methacrylate. In particular, it is also possible with advantage to use mixtures resulting from the industrial preparation. Thus, for example, industrially prepared hydroxypropyl methacrylate is composed of about 20%-30% 3-hydroxypropyl methacrylate and 70%-80% 2-hydroxypropyl methacrylate.

As further monomer units for the synthesis of the poly(meth)acrylate polyols it is possible to use alkyl(meth)acrylates, such as, ethyl acrylate, ethyl methacrylate, propyl acrylate, propyl methacrylate, isopropyl acrylate, isopropyl methacrylate, butyl acrylate, butyl methacrylate, isobutyl acrylate, isobutyl methacrylate, tert-butyl acrylate, tert-butyl methacrylate, amyl acrylate, amyl methacrylate, hexyl acrylate, hexyl methacrylate, ethylhexyl acrylate, ethylhexyl methacrylate, 3,3,5-trimethylhexyl acrylate, 3,3,5-trimethylhexyl methacrylate, stearyl acrylate, stearyl methacrylate, lauryl acrylate or lauryl methacrylate, cycloalkyl acrylates and/or cycloalkyl methacrylates, such as cyclopentyl acrylate, cyclopentyl methacrylate, isobornyl acrylate, isobornyl methacrylate or, in particular, cyclohexyl acrylate and/or cyclohexyl methacrylate.

As further monomer units for the synthesis of the poly(meth)acrylate polyols it is possible to use vinylaromatic hydrocarbons, such as vinyltoluene, alpha-methylstyrene or, in particular, styrene, amides or nitriles of acrylic or methacrylic acid, vinyl esters or vinyl ethers, and also, in minor amounts, in particular, acrylic and/or methacrylic acid.

Suitable polyester polyols are described in EP-A-0 994 117 and EP-A-1 273 640, for example. In particular, it is possible to obtain suitable polyester polyols, as is known to a person of ordinary skill in the art, through polycondensation from polyols and polycarboxylic acids or their anhydrides.

Particularly suitable as polyol or polyol mixture which can be used in the polycondensation reaction are polyhydric alcohols and mixtures thereof, the alcohols having at least two, preferably at least three, hydroxyl groups. In one or more embodiments, the polyol mixture used or the polyol used comprises or is at least one polyfunctional polyol containing at least three hydroxyl groups. Suitable polyfunctional polyols having at least three hydroxyl groups are selected from the group consisting of trimethylolpropane (TMP), trimethylolethane (TME), glycerol, pentaerythritol, sugar alcohols, ditrimethylolpropane, dipentaerythritol, diglycerol, trishydroxyethyl isocyanurate and mixtures thereof. In one specific embodiment the polyol used for preparing the polyester polyols is composed only of polyfunctional polyols having more than three hydroxyl groups. In another specific embodiment, the polyol mixture used for preparing the polyester polyols comprises at least one polyfunctional polyol having at least three hydroxyl groups and at least one diol. Examples of suitable diols include ethylene glycol, propylene glycol, butane-1,4-diol, pentane-1,5-diol, hexane-1,6-diol, neopentyl glycol, 2-butyl-2-ethylpropane-1,3-diol, diethylene glycol, dipropylene glycol, higher polyether diols, dimethylolcyclohexane, and mixtures of the aforementioned polyols.

Polycarboxylic acids or anhydrides thereof that are suitable for preparing the polyester polyols are, for example, phthalic acid, phthalic anhydride, isophthalic acid, terephthalic acid, trimellitic acid, trimellitic anhydride, pyromellitic acid, pyromellitic dianhydride, tetrahydrophthalic acid, 1,2-, 1,3- or 1,4-cyclohexanedicarboxylic acid, 1,2-cyclohexanedicarboxylic anhydride, tricyclodecanedicarboxylic acid, succinic acid, glutaric acid, adipic acid, pimelic acid, suberic acid, azelaic acid, sebacic acid, maleic acid, maleic anhydride, fumaric acid, itaconic acid, mesaconic acid, citraconic acid, dimer fatty acids and mixtures thereof. In one specific embodiment polycarboxylic acids of class 1 below are used exclusively for preparing the polyester polyols that are employed in the present invention. Class 1 consists of phthalic acid, phthalic anhydride, isophthalic acid, terephthalic acid, trimellitic acid, trimellitic anhydride, pyromellitic acid, pyromellitic dianhydride, tetrahydrophthalic acid, tetrahydrophthalic anhydride, hexahydrophthalic acid, hexahydrophthalic anhydride and mixtures thereof.

In another specific embodiment the polyester polyols used in the present invention are prepared using at least 50% by weight, based on the total weight of the polycarboxylic acid component, of polycarboxylic acids or anhydrides thereof from class 1. According to this embodiment, the polycarboxylic acid component is composed of not more than 50% by weight, based on its total weight, of at least one polycarboxylic acid of class 2 below, consisting of succinic acid, glutaric acid, adipic acid, pimelic acid, suberic acid, azelaic acid, sebacic acid, dimer fatty acids and mixtures thereof. According to this embodiment, the polycarboxylic acid component may in addition to at least one polycarboxylic acid from class 1 and optionally at least one polycarboxylic acid from class 2 further contain up to a maximum of 10% by weight of at least one polycarboxylic acid from class 3, consisting of maleic acid, maleic anhydride, fumaric acid, itaconic acid, mesaconic acid, citraconic acid and mixtures thereof.

In one or more embodiments, suitable polyurethane polyols are prepared, as is known to a person of ordinary skill in the art, by reaction of polyester polyol prepolymers—including, for example, those of the aforementioned type—with suitable di- or polyisocyanates, and are described in EP-A-1 273 640, for example.

Suitable polysiloxane polyols are described in WO-A-01/09260, for example, the polysiloxane polyols recited therein being employed in combination with other polyols, more particularly those having relatively high glass transition temperatures.

Where the coating material composition of the invention further comprises additional binders, apart from the binders which may be subsumed under the term of the polymeric polyols (a), then these other binders may react with the other components of the coating material or else be chemically inert with respect to said components.

In one or more embodiments, physically drying binders—that is, binders that are inert chemically with respect to the other paint constituents—are, for example, cellulose acetobutyrate (CAB), polyamides or polyvinyl butyral.

"Aliphatic polyisocyanates" of component (b) are understood to be compounds having at least two free, specifically at least three free, isocyanate groups in the molecule—that is, isocyanate groups which are not blocked at room temperature (25° C.). The term "aliphatic polyisocyanates" also comprehends dimers, trimers and polymers of the aliphatic polyisocyanates. Examples thereof are dimers, trimers and polymers of hexamethylene diisocyanate (HDI), including for example its uretdiones and more particularly its isocyanurates.

The coating material of the invention may also comprise further crosslinkers besides the aforementioned aliphatic polyisocyanates. Besides the aliphatic polyisocyanates there may also be used, in particular, cycloaliphatic polyisocyanates, such as more particularly isophorone diisocyanate (IPDI) and its dimers, trimers and polymers, or cyclohexane (bis-alkyl isocyanate) and also the dimers, trimers and polymers thereof. The use of aromatic polyisocyanates, in contrast, is less preferred, since coatings obtained from coating materials comprising aromatic polyisocyanates tend toward yellowing. In one particular embodiment of the invention, therefore, no aromatic polyisocyanates are used in the coating material.

In one or more embodiments, as aliphatic unblocked polyisocyanates it is especially preferred to use the trimers of HDI, of the kind obtainable, for example, as Basonat HI 100 from BASF SE (Ludwigshafen, Germany), as Desmodur® N 3300 and Desmodur® XP 2410 from Bayer Material Science AG (Leverkusen, Germany), or as Tolonate® HDT and HDB from Perstorp AB in Perstorp, Sweden, and also similar products from Asahi Kasei Chemicals, Kawasaki, Japan, trade name Duranate® TLA, Duranate® TKA or Duranate® MHG.

In minor amounts it is also possible to use crosslinkers different from the abovementioned polyisocyanates (b). Especially advantageous in this context are those which enter into curing reactions with the binders within the same temperature range as the aliphatic polyisocyanates (b). Examples of suitable such crosslinkers include components containing silyl groups, of the kind specified in WO 2008/074489, WO 2008/074490 and WO 2008/074491.

In one or more embodiments, the glycerol diester component (c) of the invention is present in the coating material compositions of the invention in an amount of 2% to 20% by weight, more specifically in an amount of 3% to 18% by weight, very specifically in an amount of 5% to 15% by weight or even better 8% to 15% by weight, based on the total weight of components (a) and (c) in the coating material composition. Where the fraction of the glycerol diester component (c) is below 2% by weight, based on the total weight of components (a) plus (c), the effect according to the invention is usually small. Where the fraction of the glycerol diester component (c) is above 20% by weight, based on the total weight of components (a) plus (c), the result is frequently inadequately crosslinked films possessing deficient resistance properties.

As well as the components (a), (b) and (c), which are necessarily present in the coating material, it is possible, as already mentioned above, for further—different—crosslinkers, binders or reactive diluents to be present in the coating material.

In particular the compositions may also comprise solvents. Suitable solvents include all typical paint solvents such as, more particularly, aromatic hydrocarbons or butyl acetate.

Furthermore, the coating materials may also comprise further typical paint additives, different from components (a), (b) and (c), such as, for example, catalysts of the crosslinking reaction(s), light stabilizers, preservatives, leveling additives, antisag agents (for example, those known as sag control agents), wetting agents, matting agents, dyes, pigments or fillers.

In one or more embodiments, the coating material composition of the invention is a clearcoat material—that is, it is free or substantially free from nontransparent pigments and fillers.

In one or more embodiments, the coating material composition of the invention is employed with as the uppermost paint coat in a multicoat paint system. In specific embodiments, it is applied as a clearcoat in automobile bodywork finishing or in the finishing of automobile bodywork parts. Since the compositions of the invention cure chemically even at low temperatures (generally even below 100° C.), they can be used in specific embodiments in automotive refinishing.

In one or more embodiments, the coating material composition of the invention is prepared shortly before its application, by mixing of the components, since a crosslinking reaction between the free isocyanate groups of the aliphatic polyisocyanate (b) and the hydroxyl groups present in the polymeric polyol (a) and in the glycerol diester (c) may take place even at room temperature. Preliminary mixing of the polymeric polyols (a) with the glycerol diester or diesters (c) generally presents no problems. In each case, the constituents of the coating material composition that are reactive with one another ought to be mixed not until shortly before the application of the coating material, in order to ensure a maximum processing life.

The present invention further provides a multicoat paint system comprising at least two coats, specifically at least three coats. The coats are disposed on a primed or unprimed substrate, with the uppermost coat being formed from a coating material composition of the invention. If the substrate is primed, then the primer, in one or more embodiments, is an electrodeposition primer, more particularly a cathodic electrodeposition primer. Priming may also, in particular, be preceded by a phosphatizing treatment.

Atop the primed or unprimed substrate there may be, for example, an applied conventional primer-surfacer coating material. To the primer-surfacer coating material—when present—there may be one or more basecoats applied. In the case of automotive refinishing, the basecoats in question are typically those which dry purely physically or those which cure thermally, by means of a crosslinker, or those which cure chemically at moderate temperatures (room temperature to 100° C.) and actinically, or actinically only. Another possibility is to furnish primer-surfacer coating materials with the properties of a basecoat or, conversely, to furnish a basecoat with primer-surfacer properties, with the consequence that it may be sufficient to apply only one primer-surfacer coat or only one basecoat. Typically a primer-surfacer coating material is applied as primer-surfacer coat, and at least one basecoat composition is applied as basecoat.

Suitability as primer-surfacer coating material and as basecoat composition is possessed by all commercial primer-surfacers or basecoat materials, more particularly those as used in automotive refinishing. The last coat applied, finally, is a coating composition of the invention as a topcoat, specifically as a transparent topcoat (clearcoat).

Additionally provided by the invention, accordingly, is a method for producing a multicoat paint system of the invention, comprising the following steps:
(i) applying a primer-surfacer coating material to an untreated or pretreated substrate and/or
(ii) applying at least one basecoat composition thereto and subsequently
(iii) applying at least one coating material composition of the invention, more particularly a topcoat composition, specifically in the form of a clearcoat material, followed by
(iv) curing of the multicoat paint system at a temperature up to 100° C. maximum.

As primer-surfacer coating material and basecoat composition it is possible to use conventional, commercial primer-surfacers and basecoat materials. Especially suitable are those as used in automotive refinishing.

The individual coats are applied by the customary painting methods familiar to a person of ordinary skill in the art. The compositions and coating materials are applied specifically by spraying, pneumatically and/or electrostatically.

In one or more embodiments, steps (i), (ii) and (iii) take place wet-on-wet. Prior to the application of the basecoat composition or basecoat compositions, the primer-surfacer may merely be flashed off at room temperature, or else, alternatively, it may be dried at elevated temperature of 100° C. maximum, more specifically 30 to 80° C. and very specifically 40 to 60° C. Drying may also take place by IR irradiation.

The comments made above in relation to the primer-surfacer coating system, with regard to the flashing and/or drying and the associated drying temperatures, also apply equally to the basecoat or basecoats.

Instead of a wet-on-wet application, a further possibility is the curing of the primer-surfacer and/or basecoat coat or coats prior to the application of the coat in step (iii). The conventional primer-surfacers and/or basecoat materials can be cured thermally, with actinic radiation, or with a combination of thermal curing and actinic radiation curing.

The curing of the clearcoat takes place likewise at temperatures up to 100° C. maximum, more specifically at temperatures from room temperature to 80° C. maximum, and very specifically at temperatures from 30 to 60° C. Curing may also be preceded by flashing.

Additionally provided by the present invention is a substrate on which a multicoat paint system of the invention is applied.

Suitable substrate materials include, in particular, metallic substrates, such as automobile bodywork or automobile bodywork parts, for example, but also plastics substrates, of the kind used in particular in the two-component OEM finishing of plastics parts.

The invention is illustrated below by examples.

EXAMPLES

The experiments below were carried out using reagents and solvents in technical purity from various manufacturers. Cardura® E10 and Versatic acid were obtained from Hexion (Louvain-la-Neuve, Belgium). The size exclusion GPC was carried out using the Isocratic Mode Pump Waters 515 and the HR5E (linear) and HR2 (500) columns in series (from Waters, Eschborn, Germany and PSS Polymer Standard Services Mainz, Germany). The polystyrene standard used was Calibration Polystyrene PS2 from Polymer Laboratories (Darmstadt, Germany) (580 to 377400 Da). The Gardner viscosity was determined using standard Gardner tubes (from Byk Gardner, Geretsried, Germany) and the Brookfield viscosity using the CAP 2000 instrument (Brookfield E.L.V. GmbH, Lorch, Germany). DOI measurements were carried out using the wave-scan instrument DOI 4816 from Byk Gardner (Geretsried, Germany).

Example 1

Preparation of an Inventive Glycerol Diester

A 5 liter reaction vessel equipped with a mechanical stirrer and reflux condenser was charged with 1241.1 g (7.25 mol) of Versatic acid and 1758.9 g (7.10 mol) of Cardura® E10. This initial charge was heated to 150° C. at a stirring speed of 150 revolutions per minute. The progress of reaction was monitored by determination of the acid number. After about an hour, the reaction had completed. 3000 g of a clear, pale yellowish liquid were obtained. The Gardner viscosity was I-K. The Brookfield viscosity (Cone Plate 3, 200 revolutions per minute, 23° C.) was about 325 mPas. The acid number was about 5 mg KOH/g. The color number (APHA) was 40. The number-average and weight-average molecular weights were determined by GPC against a polystyrene standard, using a refractive index detector, and were as follows: $M_w$: 450 daltons and $M_n$: 430 daltons. The ratio of primary OH groups to secondary OH groups in the target product was 1:1.27 (determined by means of $^1$H-NMR). This means that a mixture of two glycerol diesters was present (according to the definition above, the fraction of compounds with $R^1$=H was 44% and the fraction of compounds with $R^2$=H was 56%).

Example 2

Preparation of an Inventive Glycerol Diester (In Situ)

First of all, in a 6 liter reaction vessel equipped with a mechanical stirrer, a mixture of 225.6 g (0.91 mol) of Cardura® E10 [CAS 26761-45-5], 159.2 g (0.93 mol) of Versatic acid [CAS 26896-20-8] and 680.5 g of butyl acetate was heated to 160° C. in the presence of 5.0 g (0.01 mol) of triisodecyl phosphite as catalyst under a nitrogen atmosphere (2.5 bar) and with stirring (150 revolutions per minute).

The various reagents were subsequently supplied via an HPLC pump: a first quantity of di-tert-butyl peroxide (6.8 g, 0.05 mol) as initiator in 30.0 g of butyl acetate, then, after 15 minutes, over a period of 4 hours at 160° C., a homogeneous mixture of 522.8 g (5.22 mol) of methyl methacrylate, 1215.8 g (11.69 mol) of styrene, 30.4 g (0.24 mol) of butyl acrylate, 249.2 g (1.75 mol) of butyl methacrylate, 30.4 g (0.42 mol) of acrylic acid and 990.5 g (7.61 mol) of hydroxyethyl methacrylate and also a further 103.0 g (0.70 mol) of di-tert-butyl peroxide and 77.0 g of butyl acetate were introduced. Thereafter, over a period of 30 minutes, a further 13.6 g (0.10 mol) of di-tert-butyl peroxide in 20.0 g of butyl acetate were added, in order to ensure complete reaction of the monomers. The reaction mixture was cooled to 100° C. while pressure compensation to atmospheric pressure took place, and was diluted with 760.0 g of methyl isobutyl ketone to give 5000.0 g of a clear, colorless and viscous solution of the polymer. The solids amounts to about 72% (1 g was dried at 110° C. for 1 hour). The hydroxyl-functional poly(meth)acrylate obtained possesses an acid number of about 14 mg KOH/g, a hydroxyl number of 140 mg KOH/g, a number-average molecular weight $M_n$ of 1920 g/mol (determined by means of gel permeation chromatography (GPC) against a polystyrene standard) and a weight-average molecular weight $M_w$ of 3680 g/mol (determined by means of GPC against a polystyrene standard). The Gardner viscosity was Z-Z2 and the Brookfield viscosity (Cone Plate 3, 50 revolutions per minute, 23° C.) was about 11 200 mPas.

Example 3

Preparation of a Hydroxyl-Functional Poly(Meth)Acrylate

First of all, in a 6 liter reaction vessel equipped with a mechanical stirrer, 727.3 g of butyl acetate were heated to 160° C. under a nitrogen atmosphere (2.5 bar) and with stirring (150 revolutions per minute).

The various reagents were subsequently supplied via an HPLC pump: a first quantity of di-tert-butyl peroxide (8.5 g, 0.06 mol) as initiator in 30.0 g of butyl acetate, then, after 15 minutes, over a period of 4 hours at 160° C., a homogeneous mixture of 574.5 g (5.74 mol) of methyl methacrylate, 1336.0 g (12.85 mol) of styrene, 33.4 g (0.26 mol) of butyl acrylate, 273.9 g (1.92 mol) of butyl methacrylate, 33.4 g (0.46 mol) of acrylic acid and 1088.4 g (8.36 mol) of hydroxyethyl methacrylate and also a further 135.1 g (0.92 mol) of di-tert-butyl peroxide and 113.6 g of butyl acetate were introduced. Thereafter, over a period of 30 minutes, a further 17.0 g (0.12 mol) of di-tert-butyl peroxide in 20.0 g of butyl acetate were added, in order to ensure complete reaction of the monomers. The reaction mixture was cooled to 100° C. while pressure compensation to atmospheric pressure took place, and was diluted with 680.0 g of methyl isobutyl ketone to give 5050.0 g of a clear, colorless and viscous solution of the polymer. The solids amounts to about 72% (1 g was dried at 110° C. for 1 hour). The hydroxyl-functional poly(meth)acrylate obtained possesses an acid number of about 14 mg KOH/g, a hydroxyl number of 126 mg KOH/g, a number-average molecular weight $M_n$ of 2260 g/mol (determined by means of gel permeation chromatography (GPC) against a polystyrene standard) and a weight-average molecular weight $M_w$ of 4750 g/mol (determined by means of GPC against a polystyrene standard). The Gardner viscosity was Z1-Z3 and the Brookfield viscosity (Cone Plate 3, 50 revolutions per minute, 23° C.) was about 6350 mPas.

Use Examples 1 (Comparative) and 1A (Inventive)

In accordance with table 1 below, coating material compositions were produced (use example 1 (noninventive) and use example 1A (inventive)).

TABLE 1

|  | Use example 1 (parts by weight) | Use example 1A (parts by weight) |
|---|---|---|
| Composition from example 2 (glycerol diester incl. poly(meth)acrylate) | — | 78 |
| Composition from example 3 (poly(meth)acrylate only) | 78 | — |
| Benzoic acid | 1.5 | 1.5 |
| Dibutyltin dilaurate | 0.18 | 0.18 |
| Light stabilizer comprising HALS and UV absorber | 2.2 | 2.2 |

TABLE 1-continued

|  | Use example 1 (parts by weight) | Use example 1A (parts by weight) |
|---|---|---|
| Polyester-modified polymethyl-alkylsiloxane | 0.3 | 0.3 |
| Solvent mixture (aromatic solvents and esters) | 16.2 | 16.2 |
| Solids (1 g, 1 hour, 110° C.) | 60% | 60% |
| Curing agent 929.33 (Glasurit GmbH) | 49.2 | 49.2 |
| Diluent 352-91 (Glasurit GmbH) | 8.5 | 8.5 |
| Solids (1 g, 1 hour, 110° C.) | 56% | 56% |

The clearcoat material of noninventive use example 1 possessed an efflux viscosity by the DIN4 cup method of 20 s. Clearcoat material 1A (inventive) was given the same amount of diluent, but gave an efflux viscosity of only 18 s in the DIN4 cup. The solids content (1 g, 110° C., 1 h) was found for both clearcoat mixtures to be 56%.

Metal panels coated beforehand with a coil primer and measuring 40×60 cm were coated initially with a commercial primer-surfacer (Glasurit 285-31) and with an aqueous basecoat material (Glasurit, 90 line, jet black). The basecoat was subjected to preliminary drying in a forced-air oven at 60° C. for 10 minutes. The clearcoat materials of use examples 1 and 1A were subsequently applied by means of pneumatic spray application (SATA HVLP) with a resultant dry film thickness of 61 micrometers (clearcoat 1) or 59 micrometers (clearcoat 1A). After a flash-off phase at RT for 10 minutes, for which the panels were suspended vertically, the panels, still hanging vertically, are dried at 60° C. for 30 minutes.

After that, the appearance was ascertained. With virtually identical dry film thickness and virtually identical distinctness of image (DOI) (84.3 (use example 1) and 84.2 (use example 1A)), the Wavescan results are significantly different. The coating comprising the coating material of the invention possesses significantly better values, in both the longwave and shortwave regions, than the coating comprising the noninventive coating material (longwave (inventive): 20.7, longwave (noninventive): 27.1; shortwave (inventive): 15.1, shortwave (noninventive): 18.6). This demonstrates significantly better leveling of the finishes of the invention with virtually the same or even a somewhat lower film thickness. In addition, the clearcoat material of the invention, while having the same solids content, possesses the advantage of a lower viscosity.

What is claimed is:

1. A method of preparing a composition, the method comprising adding a reactive diluent comprising a glycerol diester of general formula (I)

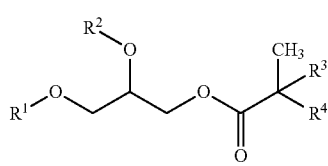

(I)

wherein one of the two radicals $R^1$ or $R^2$ is hydrogen, and the radical of the two radicals $R^1$ and $R^2$ that is not hydrogen is a radical

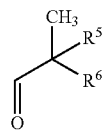

and the radicals $R^3$, $R^4$, $R^5$, and $R^6$ independently of one another are a saturated, aliphatic radical having 1 to 20 carbon atoms, with the proviso that the radicals $R^3$ and $R^4$ together contain at least 5 carbon atoms and the radicals $R^5$ and $R^6$ together contain at least 5 carbon atoms to a coating material composition, adhesive or sealant which contains a polymeric polyol and a cross-linking agent and/or a binder, wherein the glycerol diester is added in an amount of 2-20% by weight based on the total weight of the polymeric polyol and the glycerol diester in the coating material composition.

2. The method of claim 1, wherein the coating material composition is a clearcoat material.

3. A coating material composition comprising
   (a) at least one polymeric polyol selected from the group consisting of poly(meth)acrylate polyols, polyester polyols, polyurethane polyols, and polysiloxane polyols,
   (b) at least one aliphatic polyisocyanate and
   (c) at least one glycerol diester of the general formula (I)

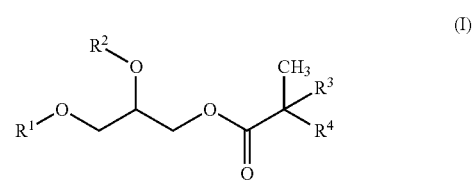

(I)

wherein
one of the two radicals $R^1$ or $R^2$ is hydrogen and the radical of the two radicals $R^1$ and $R^2$ that is not hydrogen is a radical

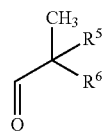

and
the radicals $R^3$, $R^4$, $R^5$ and $R^6$ independently of one another are a saturated, aliphatic radical having 1 to 20 carbon atoms,
with the proviso that the radicals $R^3$ and $R^4$ together contain at least 5 carbon atoms and the radicals $R^5$ and $R^6$ together contain at least 5 carbon atoms,
wherein the fraction of the glycerol diester component (c) is 2-20% by weight, based on the total weight of the polymeric polyol component (a) and the glycerol diester component (c) in the coating material composition.

4. The coating material composition of claim 3, wherein (a) comprises at least one poly(meth)acrylate polyol.

5. The coating material composition of claim 3, wherein the hydroxyl number of component (a) differs by not more than 20% from the hydroxyl number of the glycerol diester component (c) used in the coating material composition.

6. A multicoat paint system comprising at least two coats which are disposed on a substrate, wherein the uppermost coat of the at least two coats is composed of the coating material composition of claim 3.

7. A substrate that has been coated with the multicoat paint system of claim 6.

8. A method for producing a multicoat paint system, the method comprising:
  (i) applying a primer-surfacer coating material to an untreated or pretreated substrate and applying at least one basecoat composition thereto, or
  (ii) applying at least one basecoat composition to an untreated or pretreated substrate; and subsequently
  (iii) applying at least one clearcoat composition, the clearcoat composition comprising the coating composition of claim 3, followed by
  (iv) curing of the multicoat paint system at a temperature of up to 100° C. maximum.

9. The method of claim 8, wherein step (iv) is carried out at a temperature of 30 to 60° C.

10. A substrate that has been coated by the method of claim 8.

* * * * *